(12) United States Patent
De Prisco et al.

(10) Patent No.: US 9,285,301 B2
(45) Date of Patent: Mar. 15, 2016

(54) DIGITAL ROCK ANALYSIS SYSTEMS AND METHODS WITH RELIABLE MULTIPHASE PERMEABILITY DETERMINATION

(75) Inventors: Giuseppe De Prisco, Houston, TX (US); Jonas Toelke, Houston, TX (US)

(73) Assignee: INGRAIN, INC., Houston, TX (US)

( * ) Notice: Subject to any disclaimer, the term of this patent is extended or adjusted under 35 U.S.C. 154(b) by 751 days.

(21) Appl. No.: 13/549,354

(22) Filed: Jul. 13, 2012

(65) Prior Publication Data
US 2014/0019054 A1    Jan. 16, 2014

(51) Int. Cl.
*G01N 15/08* (2006.01)

(52) U.S. Cl.
CPC .................................... *G01N 15/082* (2013.01)

(58) Field of Classification Search
CPC ..................... G01N 2015/0833; G01N 15/082
USPC ........................................................... 702/12
See application file for complete search history.

(56) References Cited

U.S. PATENT DOCUMENTS

| | | | |
|---|---|---|---|
| 6,516,080 B1 * | 2/2003 | Nur | 382/109 |
| 2009/0288880 A1 | 11/2009 | Wojcik et al. | |
| 2010/0128932 A1 | 5/2010 | Dvorkin et al. | |
| 2010/0135536 A1 * | 6/2010 | Dvorkin et al. | 382/109 |
| 2011/0004447 A1 * | 1/2011 | Hurley et al. | 703/1 |
| 2012/0179436 A1 | 7/2012 | Fung | |

FOREIGN PATENT DOCUMENTS

WO    2014/011448    1/2014

OTHER PUBLICATIONS

Lukas M. Keller, Pore space relevant for gas permeability in Opalinus clay: Statistical analysis of homogeneity, percolation, and representative volume element, Journal of Geophysical Research: Solid Earth, vol. 118, 1-14, doi:10.1002/jgrb.50228, 2013.*

De Prisco, Giuseppe et al., "Digital Rock Analysis Systems and Methods with Multiphase Flow REV Determination", U.S. Appl. No. 13/524,758, filed Jun. 15, 2012, 22 pgs.

De Prisco, Giuseppe et al., "Method for Simulating Fractional Multi-Phase/Multi-Component Flow Through Porous Media" U.S. Appl. No. 61/506,680, filed Jul. 12, 2011, 73 pgs.

(Continued)

*Primary Examiner* — Tung S Lau
*Assistant Examiner* — Xiuquin Sun
(74) *Attorney, Agent, or Firm* — Krueger Iselin LLP (57) ABSTRACT

The pore structure of rocks and other materials can be determined through microscopy and subjected to digital simulation to determine the properties of multiphase fluid flows through the material. To ensure reliable results, the digital rock model is first analyzed via a series of operations that, in some embodiments, include: obtaining a three-dimensional pore/matrix model of a sample; determining a flow axis; verifying that the dimension of the model along the flow axis exceeds that of a representative elementary volume (REV); selecting a flow direction; extending model by mirroring if pore statistics at a given saturation are mismatched for different percolating phases; and increasing resolution if the smallest nonpercolating sphere dimension is below a predetermined threshold. This sequence of operations increases reliability of results when measuring relative permeability using the model and displaying relative permeability measurements to user.

18 Claims, 6 Drawing Sheets

(56) References Cited

OTHER PUBLICATIONS

Hilpert, Markus et al., "Pore-Morphology-Based Simulation of Drainage in Totally Wetting Porous Media", Advances in Water Resources 24 (2001) 243-255, 13 pgs.

Papatzacos, Paul "Cellular Automation Model for Fluid Flow in Porous Media", Complex Systems 3 (1989) pp. 383-405, 23 pgs.

PCT International Search Report and Written Opinion, dated Dec. 19, 2013, Appl No. PCT/US2013/049113, "Digital Rock Analysis system and methods with realiable multiphase permeability determination," filed Jul. 2, 2013, 14 pgs.

PCT International Preliminary Report on Patentability, dated Jan. 22, 2015, Appl No. PCT/US2013/049113, "Digital Rock Analysis system and methods with realiable multiphase permeability determination," filed Jul. 2, 2013, 8 pgs.

Adalsteinsson, David, et al., "Accurate and Efficient Implementation of Pore-Morphology-based Drainage Modeling in Two-dimensional Porous Media," Transport in Porous Media (2006) 65: 337-358, © Springer 2006, 22 pgs., DOI 10.1007/s11242-005-6091-6.

Hazlett, R. D., "Simulation of Capillary-Dominated Displacements in Microtomographic Images of Reservoir Rocks," Transport in Porous Media 20:21-35, 1995, 15 pgs., KluwerAcademic Publishers. Printed in the Netherlands.

\* cited by examiner

DIGITAL ROCK ANALYSIS SYSTEMS AND METHODS WITH RELIABLE MULTIPHASE PERMEABILITY DETERMINATION

BACKGROUND

Microscopy offers scientists and engineers a way to gain a better understanding of the materials with which they work. Under high magnification, it becomes evident that many materials (including rock and bone) have a porous microstructure that permits fluid flows. Such fluid flows are often of great interest, e.g., in subterranean hydrocarbon reservoirs. Accordingly, significant efforts have been expended to characterize materials in terms of their flow-related properties including porosity, permeability, and saturation.

Scientists typically characterize materials in the laboratory by applying selected fluids with a range of pressure differentials across the sample. Such tests often require weeks and are fraught with difficulties, including requirements for high temperatures, pressures, and fluid volumes, risks of leakage and equipment failures, and imprecise initial conditions. (Flow-related measurements are generally dependent not only on the applied fluids and pressures, but also on the history of the sample. The experiment should begin with the sample in a native state, but this state is difficult to achieve once the sample has been removed from its original environment.)

Accordingly, industry has turned to digital rock analysis to characterize the flow-related properties of materials in a fast, safe, and repeatable fashion. A digital representation of the material's pore structure is obtained and used to characterize the flow-related properties of the material. However, the quality of the characterization is dependent upon the degree to which the digital representation accurately represents the physical material. A sample that is too small is unlikely to be representative of the overall material due to anisotropy and/or heterogeneities, whereas a sample that is too large will impose excessive computational demands without yielding any additional benefit. It would be desirable to have a procedure that efficiently ensures the accuracy of multiphase flow-related measurements derived from a digital rock model.

BRIEF DESCRIPTION OF THE DRAWINGS

Accordingly, there are disclosed herein digital rock analysis systems and methods with reliable determinations of multiphase permeability. In the drawings.

It should be understood, however, that the specific embodiments given in the drawings and detailed description below do not limit the disclosure. On the contrary, they provide the foundation for one of ordinary skill to discern the alternative forms, equivalents, and other modifications that are encompassed in the scope of the appended claims.

DETAILED DESCRIPTION

Figure 1:
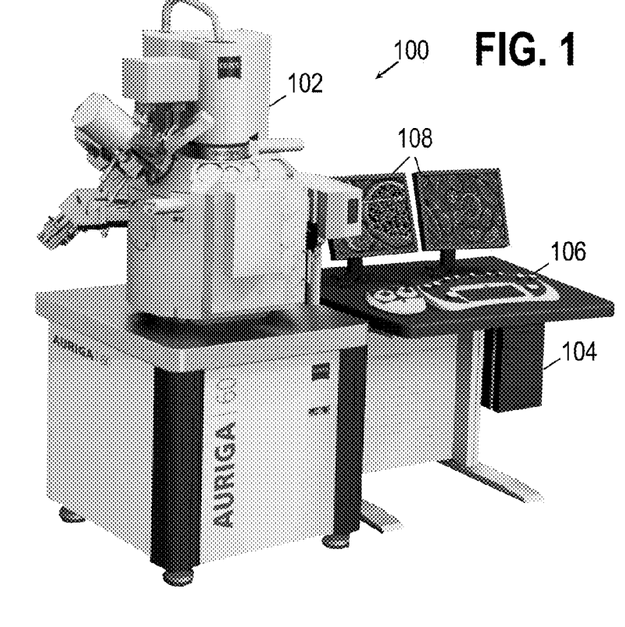
FIG. 1 shows an illustrative high resolution focused ion beam and scanning electron microscope.

For context, FIG. 1 provides an illustration of a high-resolution focused ion beam and scanning electron microscope 100 having an observation chamber 102 in which a sample of material is placed. A computer 104 is coupled to the observation chamber instrumentation to control the measurement process. Software on the computer 104 interacts with a user via a user interface having one or more input devices 106 (such as a keyboard, mouse, joystick, light pen, touchpad, or touchscreen) and one or more output devices 108 (such as a display or printer).

For high resolution imaging, the observation chamber 102 is typically evacuated of air and other gases. A beam of electrons or ions can be rastered across the sample's surface to obtain a high resolution image. Moreover, the ion beam energy can be increased to mill away thin layers of the sample, thereby enabling sample images to be taken at multiple depths. When stacked, these images offer a three-dimensional image of the sample to be acquired. As an illustrative example of the possibilities, some systems enable such imaging of a 40×40×40 micrometer cube at a 10 nanometer resolution.

The system described above is only one example of the technologies available for imaging a sample. Transmission electron microscopes (TEM) and three-dimensional tomographic x-ray transmission microscopes are two other technologies that can be employed to obtain a digital model of the sample. Regardless of how the images are acquired, the following disclosure applies so long as the resolution is sufficient to reveal the porosity structure of the sample.

The source of the sample, such as in the instance of a rock formation sample, is not particularly limited. For rock formation samples, for example, the sample can be sidewall cores, whole cores, drill cuttings, outcrop quarrying samples, or other sample sources which can provide suitable samples for analysis using methods according to the present disclosure.

Figure 2:
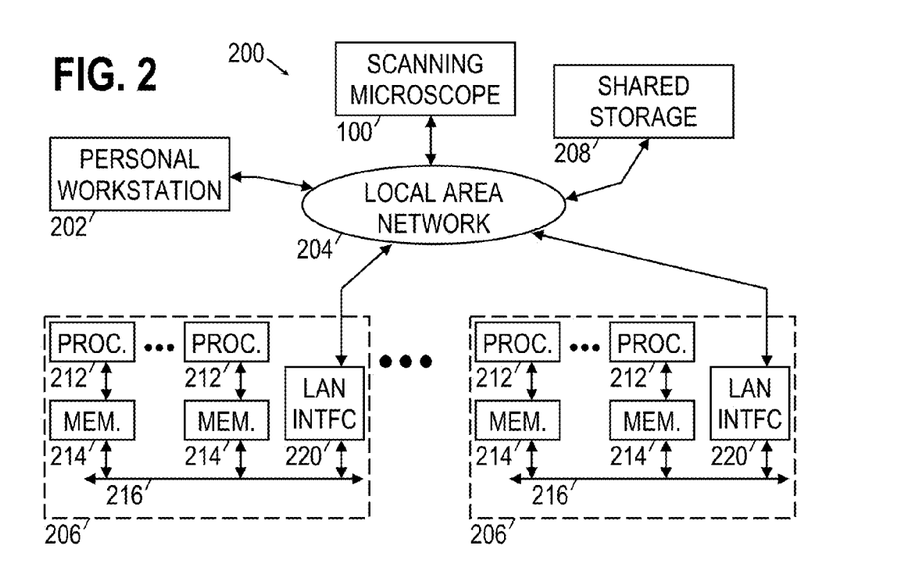
FIG. 2 shows an illustrative high performance computing network.

FIG. 2 is an example of a larger system 200 within which the scanning microscope 100 can be employed. In the larger system 200, a personal workstation 202 is coupled to the scanning microscope 100 by a local area network (LAN) 204. The LAN 204 further enables intercommunication between the scanning microscope 100, personal workstation 202, one or more high performance computing platforms 206, and one or more shared storage devices 208 (such as a RAID, NAS, SAN, or the like). The high performance computing platform 206 generally employs multiple processors 212 each coupled to a local memory 214. An internal bus 216 provides high bandwidth communication between the multiple processors (via the local memories) and a network interface 220. Parallel processing software resident in the memories 214 enables the multiple processors to cooperatively break down and execute the tasks to be performed in an expedited fashion, accessing the shared storage device 208 as needed to deliver results and/or to obtain the input data and intermediate results.

Typically, a user would employ a personal workstation 202 (such as a desktop or laptop computer) to interact with the larger system 200. Software in the memory of the personal workstation 202 causes its one or more processors to interact with the user via a user interface, enabling the user to, e.g., craft and execute software for processing the images acquired by the scanning microscope. For tasks having small computational demands, the software may be executed on the personal workstation 202, whereas computationally demanding tasks may be preferentially run on the high performance computing platform 206.

Figure 3A:
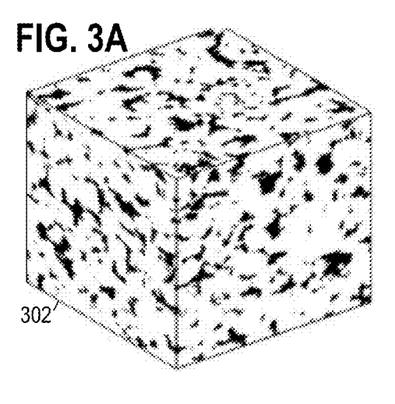
FIG. 3A shows an illustrative volumetric representation of a sample.

FIG. 3A is an illustrative image 302 that might be acquired by the scanning microscope 100. This three-dimensional image is made up of three-dimensional volume elements ("voxels") each having a value indicative of the composition of the sample at that point.

Figure 3B:
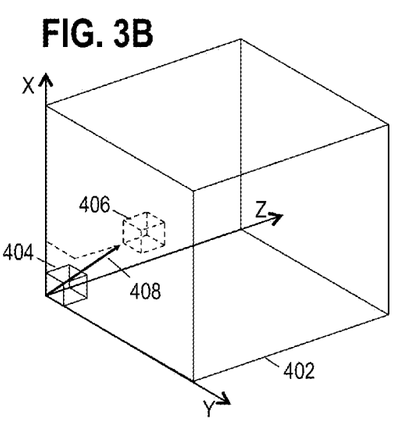
FIG. 3B shows an illustrative coordinate system for performing sample analysis.
Figure 4:
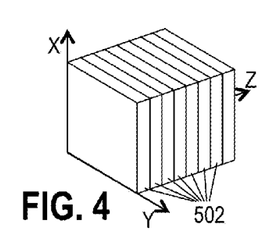
FIG. 4 shows an illustrative division of a model region into slices.

FIG. 3B provides a coordinate system for a data volume 402, with the x-, y-, and z-axes intersecting at one corner of the volume. Within the data volume, a subvolume 404 is defined. The illustrated subvolume 404 is a cube having sides of length a, but other subvolume shapes may alternatively be used, e.g., a parallelogram having the same shape as the overall data volume, a sphere, or a tetrahedron. It is desirable, though not necessary, for the chosen subvolume shape to be scalable via a characteristic dimension such as diameter or length of a side. The subvolume 404 can be defined at any position 406 within the data volume 402 using a displacement vector 408 from the origin to a fixed point on the subvolume. Similarly, sub-subvolumes can be defined and positioned within each subvolume. For example, FIG. 4 shows a subvolume divided into slices 502 perpendicular to the flow direction (in this case, the z-axis).

One way to characterize the porosity structure of a sample is to determine an overall parameter value, e.g., porosity. The image is processed to categorize each voxel as representing a pore or a portion of the matrix, thereby obtaining a pore/matrix model in which each voxel is represented by a single bit indicating whether the model at that point is matrix material or pore space. The total porosity of the sample can then be determined with a straightforward counting procedure. However, the resulting number reveals little about the structure, heterogeneity and isotropy of the sample. Accordingly, a more sophisticated measure may be preferred.

One example of a more sophisticated measure is the standard deviation of porosity along a specific direction. As shown in FIG. 4, a volume (or subvolume) can be divided into slices perpendicular to the flow direction. The structure of the pores may cause the porosity to vary from slice to slice, from which a standard deviation of porosity (relative to the average porosity) can be determined. While this measure itself provides a useful indication of the pore structure, it can be extended. If the sample volume is divided into subvolumes (see, e.g., FIG. 3B) and the standard deviation of porosity measured (relative to the average porosity of the whole sample and normalized by that same averaged porosity) for each subvolume, it yields a histogram such as that shown in FIG. 5A. Note, however, that this histogram is a function of the subvolume size. As the subvolume size grows from near zero to a representative elementary volume ("REV"), the histogram converges and becomes nearly Gaussian in shape. (By way of comparison, when the subvolume dimension in a perfectly periodic "ideal" sample has a size that is an integer multiple of the REV size, the histogram is going to have zero mean and zero variance, in other words a Dirac delta function centered at zero.)

The REV size depends on the statistical measure used to define it. The foregoing approach yields an REV suitable for Darcian analysis, and hence this REV size (e.g., diameter, length, or other dimension) is referred to herein as the "integral scale" or "Darcian scale". Other length scales may also be important to the analysis. For example, the percolation scale, defined here as the subvolume size at which the difference between total porosity and the connected porosity (porosity connected in some fashion to the inlet face) falls below a threshold, e.g., 2%. The percolation scale can be larger than, or smaller than, the integral scale.

Another measure of porosity structure is the standard deviation of surface-to-volume ratio. If the surface area (or in a two-dimensional image, the perimeter) of the pores in each slice 502 (FIG. 4) is divided by the volume (or in 2D, the surface area) of the corresponding pores, the resulting ratio exhibits some variation from slice to slice, which can be measured in terms of the standard deviation. As the standard deviation of the surface-to-volume ratio is determined for each subvolume in a model, a histogram such as that in FIG. 5B results. As before, the histogram should converge and approximate a Gaussian distribution when the subvolume size reaches or exceeds the integral scale.

Figure 6:
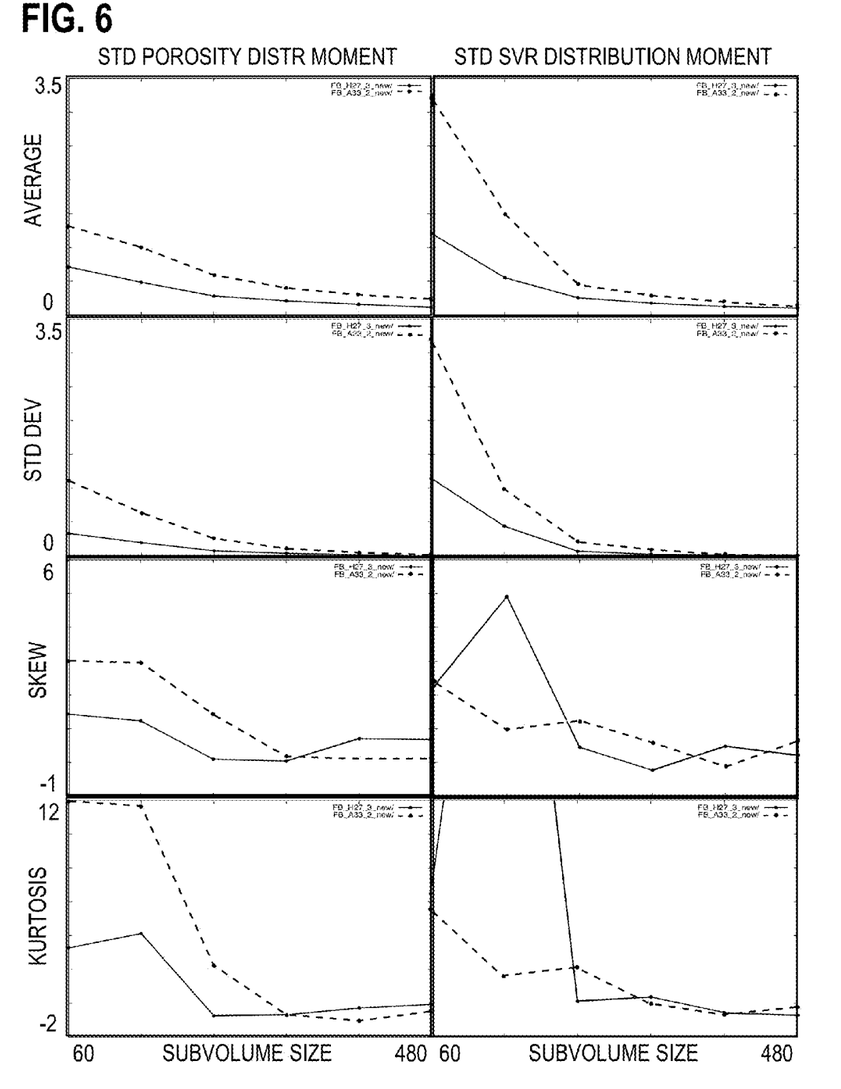
FIG. 6 illustrates a dependence of distribution moments on subvolume size.

FIG. 6 compares the moments of both histograms (standard deviation of porosity and standard deviation of surface-to-volume ratio (SVR)) for two different samples as a function of subvolume size. The first four moments (mean, standard deviation, skew, and kurtosis) are shown for subvolumes sizes as measured by edge length of the subvolume (which is a cube) in the range from 60 to 480 units. The first moment for both samples approaches zero, i.e., the center of the standard deviation of porosity and SVR distributions approaches that of the whole sample, at about 200 units, and the width of the distribution peak also approaches zero near this threshold. The second moment for both samples is similarly close to zero at this point, i.e., the probability of a subvolume having the same standard deviation of porosity and SVR as the whole sample is quite high. The asymmetry of the distribution (as indicated by the skew value) and the kurtosis also become small at and above this threshold, suggesting that the REV size, to define an integral length scale according to Darcy analysis, is no larger than 200 units. As explained in U.S. Provisional Application 61/618,265 titled "An efficient method for selecting representative elementary volume in digital representations of porous media" and filed Mar. 30, 2012 by inventors Giuseppe De Prisco and Jonas Toelke (and continuing applications thereof), either or both of these measures can be employed to determine whether reduced-size portions of the original data volume adequately represent the whole for porosity- and permeability-related analyses.

Figure 7A:
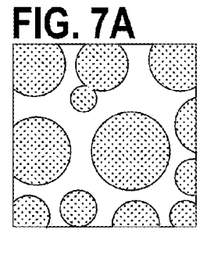
FIGS. 7A-7D illustrate a phase-based partitioning of porosity.

A potential difficulty arises, however, in analyses concerning multiple fluid phases effectively occupying different parts of the pore space. To understand why this is so, please consider FIGS. 7A-7D. FIG. 7A shows an illustrative sample image having pore space between circularly shaped grains of matrix material. Taking the white pore space as being filled with a wetting fluid phase, consider invasion by a second, non-wetting phase. In accordance with the Young-Laplace equation, a positive capillary pressure produces an interface having a constant mean curvature and curvature radii that shrink with increased pressure, yielding a pressure-related degree of invasion into the pores.

Figure 7B:
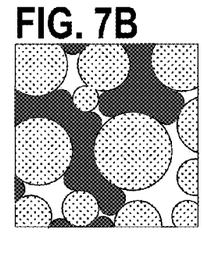
Figure 7C:
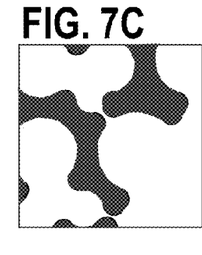
Figure 7D:
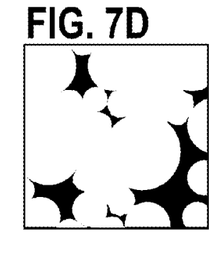

FIG. 7B shows the sample of FIG. 7A with the addition of an invading (non-wetting) fluid phase shown as black. It can be seen that the pore space has been partitioned. FIG. 7C shows the pore space filled by the non-wetting phase (in black) while FIG. 7D shows the pore space filled by the wetting phase (in black). The pore/matrix model is thus partitioned into two phase-based pore/matrix models, hereafter termed phase/matrix models. One model considers only the wetting phase and the rest is considered matrix, while the other model considers only the non-wetting phase and treats the rest as matrix. This process can be repeated for different curvature radii to generate the phase/matrix models as a function of relative saturation. More information on an illustrative partitioning process can be found in Hilpert and Miller, "Pore-morphology-based simulation of drainage in totally wetting porous media", Advances in Water Resources 24 (2001) 243-255.

The partitioning is a function of the manner (injection, drainage, imbibition), history, and degree of simulated fluid movement. In one illustrative implementation, spheres of gradually decreasing diameter, that here represent a perfect non-wetting fluid having negligible viscous coupling with the other phase, are used to invade the pore space from one or more edges of the data model. The gradually decreasing diameter enables the invading fluid to reach more of the pore space, depending on the size and connectivity. (This approach is hereafter termed the mercury injection capillary pressure ("MICP") approach because it accurately models the physical process of the same name.) In other implementations, connectivity may not be required, and fluid invasion permitted anywhere the requisite spheres will fit, the sphere diameters gradually increasing to yield less and less of the pore space to be occupied by the non-wetting fluid. (This approach is hereafter termed the Open Map approach because of its relationship to the concept of the same name taken from the field of mathematical morphology. An illustrative physical analog of this process occurs when gas comes out of solution and occupies some of the pore space.)

At each step (i.e., each sphere diameter), the saturations are determined and the corresponding phase/matrix models are determined and subject to separate analyses. For example, each phase/matrix model may be subject to a separate determination of porosity, permeability, surface-to-volume ratio, histogram of standard deviation of porosity, histogram of standard deviation of surface-to-volume ratio, and/or characteristic dimension of an REV. For example, an absolute permeability $k_{p,s}^{abs}$ can be computed from each phase/matrix model, where p is the phase (e.g., wetting or non-wetting) and s is the saturation of that phase as measured at the current invasion step in the original pore/matrix model. See, e.g., Papatzacos "Cellular Automation Model for Fluid Flow in Porous Media", Complex Systems 3 (1989) 383-405. From the computed absolute permeability values, we can obtain a (quasi static) relative permeability $k_{p,s}^{rel}=k_{p,s}^{abs}/k^{abs}$, where the denominator is the absolute permeability $k^{abs}$ of the original pore/matrix model. This calculation assumes a strong uniform wettability and negligible viscous coupling between the two phases, i.e., it represents the so-called quasi-static relative permeability.

Figure 5A:
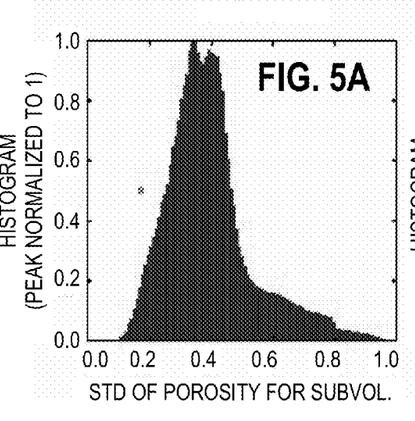
FIGS. 5A-5B show illustrative sample parameter distributions.
Figure 5B:
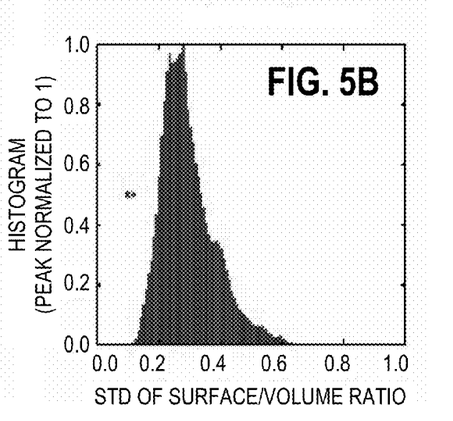
Figure 8A:
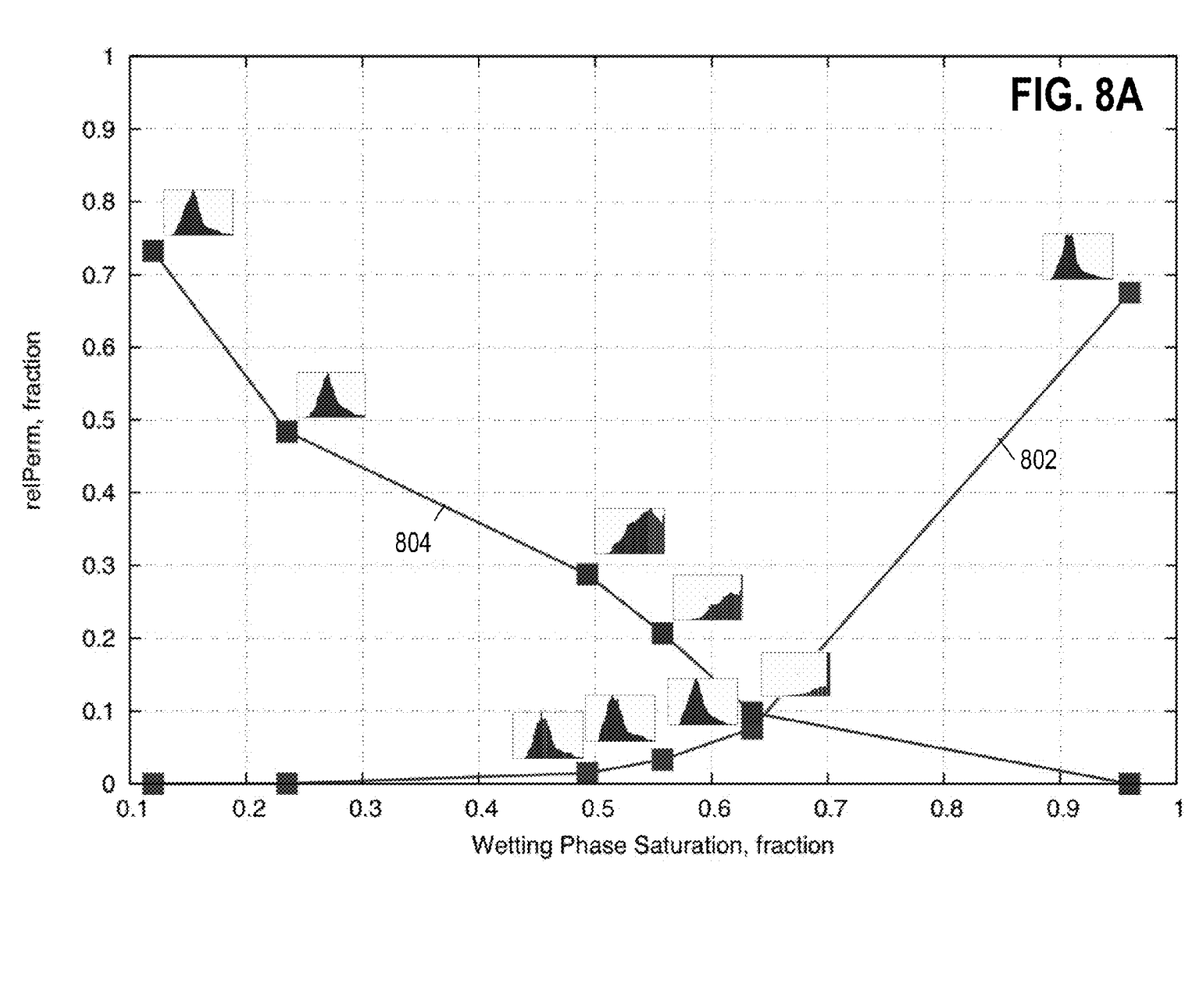
FIGS. 8A-8B show a permeability/saturation relation with parameter distributions.
Figure 8B:
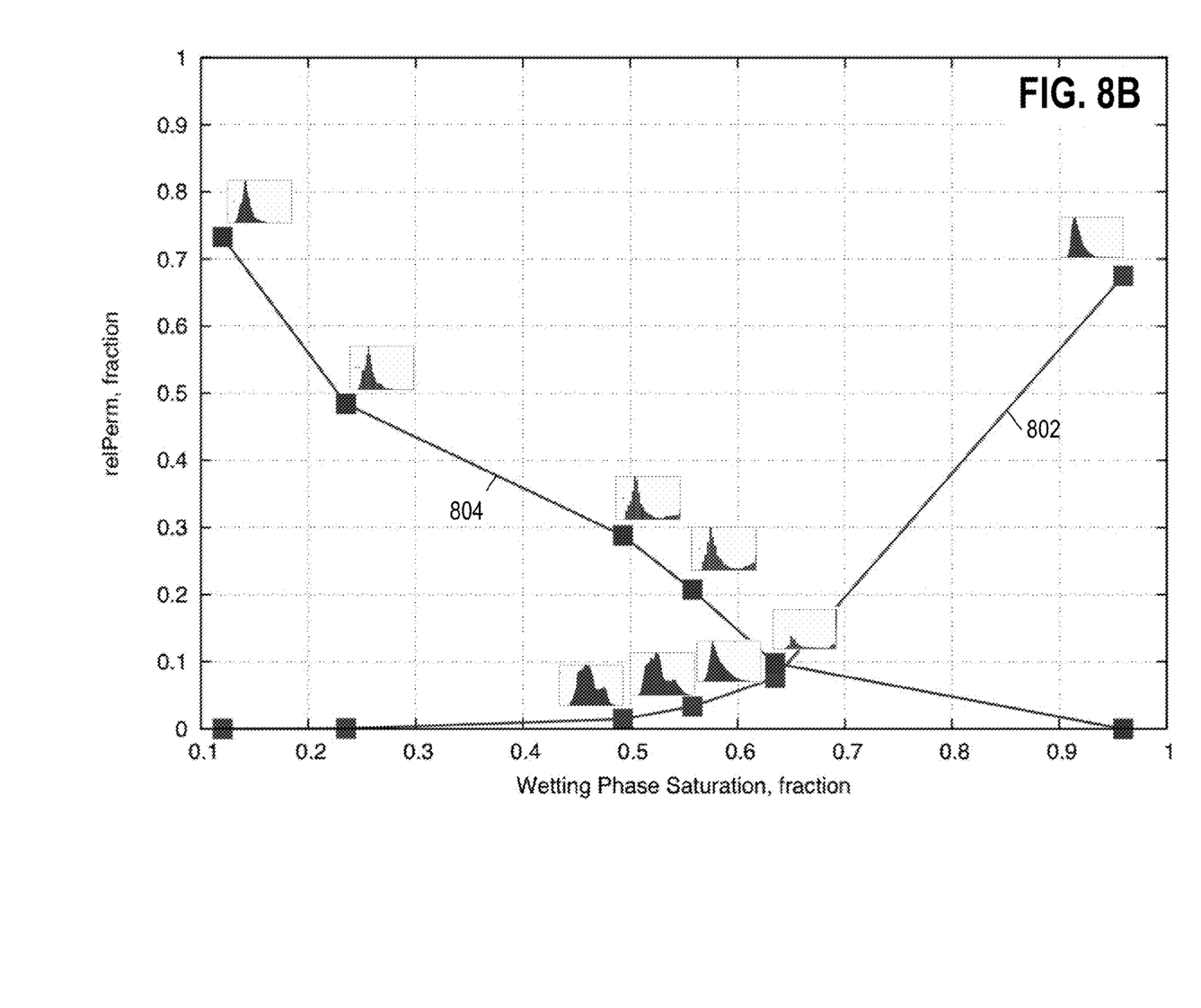

The carbonate rock sample that was used to determine the histograms in FIGS. 5A-5B was subjected to this analysis, yielding the static relative permeability vs. saturation curves shown in FIGS. 8A-8B. In both figures, curve 802 shows the quasi static relative permeability vs saturation for the wetting phase, while curve 804 shows the quasi static relative permeability vs saturation for the non-wetting phase. Insets in FIG. 8A show histograms of the standard deviation for subvolume porosity, while insets in FIG. 8B show histograms of the standard deviation for subvolume surface/volume ratio. The insets at high relative permeability values can be compared with FIGS. 5A-5B to confirm that the distributions match when the pores are largely occupied by either single phase.

As the nonwetting phase saturation falls from near 1 to about 0.5 (shown in the figure as wetting saturation near 0 and 0.5, respectively), the histogram of standard deviation of porosity broadens and moves upward, indicating greatly increased heterogeneity. In other words, the network of porosity that the non-wetting fluid is forming for lower non-wetting saturation invades only parts of the pore space, and that leads to the heterogeneous distribution. The histogram of standard deviation of surface to volume ratio and porosity shows a growing peak at the right side of the graph for the non-wetting phase curve, probably indicating the presence of large heterogeneities.

As the wetting phase saturation falls from near 1 to about 0.5, the histogram of standard deviation of porosity for the wetting phase remain a consistent match to the original distribution. This observation suggests that as soon as the wetting phase is flowing, it can access almost any part of the pore space. The histogram of standard deviation for surface-to-volume ratio, shown in FIG. 8B, acquires additional peaks, revealing the increased heterogeneity from the reduced amount of wetting phase.

Figure 9:
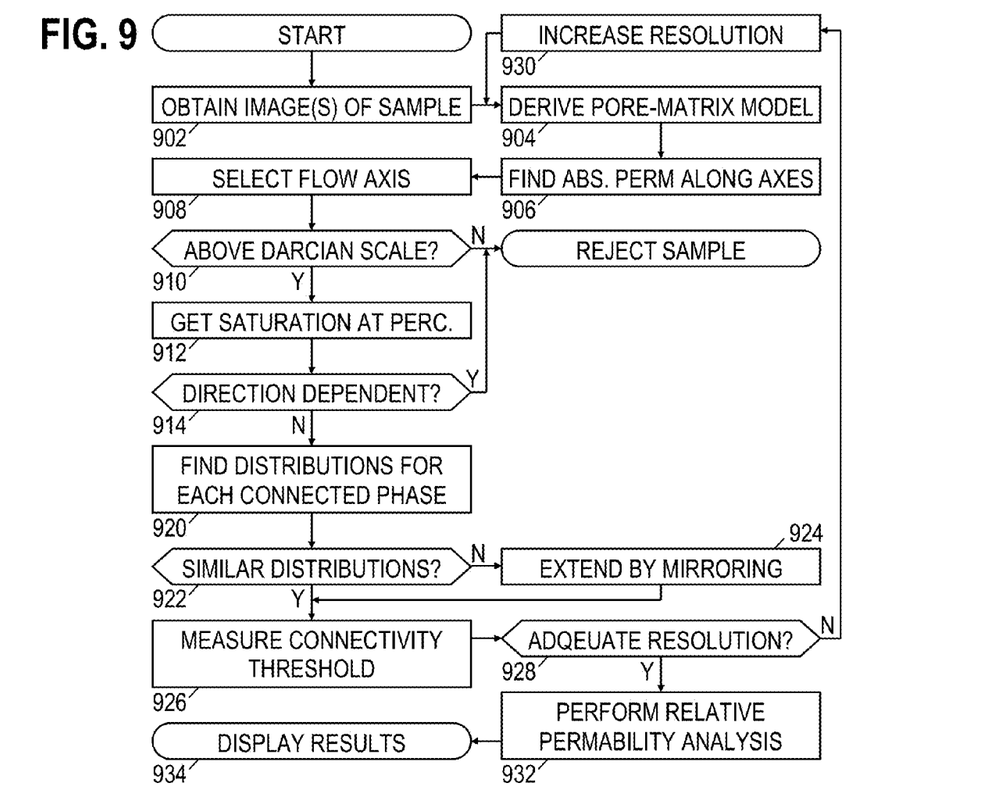
FIG. 9 is a flowchart of an illustrative analysis method.

Given the foregoing principles and practices, we turn now to a discussion of certain workflows that greatly enhance the reliability of relative permeability measurements derived from a digital rock model. FIG. 9 is an illustrative flowchart to support this discussion.

The illustrative workflow begins in block 902, where the system obtains one or more images of the sample, e.g., with a scanning microscope or tomographic x-ray transmission microscope. Of course the images can be alternatively supplied as data files on an information storage medium. In block 904, the system processes the images to derive a pore/matrix model. Such processing can involve sophisticated filtering as set forth in existing literature to classify each image voxel as representing a pore or a portion of the matrix. In block 906, the system analyzes the full pore/matrix model to obtain single phase statistics such as, e.g., porosity, surface-to-volume ratio, absolute permeability along each axis, and standard deviations of porosity and surface-to-volume ratio along each axis of the whole sample.

In block 908, the system determines a flow axis. This determination may be based on the preceding analysis or on external factors (e.g., the orientation of the material sample relative to the well, formation pressure gradients, client specifications). When the axis is not based on external factors, it may be selected based on the standard deviation of porosity: the axis having the lowest standard deviation may be preferred. Alternative bases exist and may be used.

In block 910, the system verifies that the digital model is Darcian, i.e., that the pore/matrix model is substantially larger than the Darcian length scale (the pore/matrix model is preferably at least 2-4 times larger than the REV, but at a minimum it should be at least as large as the REV). The REV size can be determined using the histograms of standard deviation of porosity and/or SVR for subvolumes of different dimensions and determining at which dimension the histograms converge to a Gaussian distribution with a small enough variance (moments analysis). If the digital model is too small, it must be rejected. In some cases, it may be possible to use the scanning microscope to process a new sample with an increased field of view.

In block 912, the system determines a direction of flow along the flow axis, i.e., which of the opposing sides perpendicular to the axis will be the inlet and which will be the outlet. A primary consideration is that the inlet face should not have any large pores (relative to the average pore size) near the boundary of the sample. Beyond that, the face with the more homogeneous distribution of pores should be preferred. The system may employ an algorithmic measure of pore homogeneity or rely on a visual inspection by the operator. In particular, the same moments analysis can be applied to 2D slices and quantitatively select the most homogeneous face.

In block 914, the system performs an MICP analysis with gradually decreasing sphere size to determine saturation A at the percolation point (i.e., the point at which the non-wetting phase is becoming connected to enable flow from the inlet to the outlet). Then the same analysis is used for the reverse flow direction to determine the saturation B at the percolation point. In block 916, the system determines whether the difference |A-B| is too large (e.g., greater than 0.2). A strong directional dependence indicates that the sample is not suitable for a relative permeability calculation and should be rejected.

In block 920, the system determines the phase/matrix model for each phase at each saturation using an MICP approach. For those phase/matrix models that are connected (percolating), the system determines the histograms of standard deviation for porosity and/or SVR. (See, e.g., FIG. 8A which shows histograms of standard deviation of porosity for each phase at different saturation values, and FIG. 8B which shows histograms of standard deviation of SVR for each phase at different saturation values.) In block 922, the system verifies for each saturation value that the histograms for the different percolating phases resemble each other (e.g., having comparable first, second and possibly higher order moments). Absent some unique features of the sample that would explain mismatch between the distributions (e.g., an unusual grain structure or heterogeneity of the sample), such mismatches could be due to boundary effects artificially introduced by the walls. The mismatch in FIGS. 8A and 8B at intermediate saturation values (S=0.5-0.7) indicates that the relative permeability measurements here are likely to be inaccurate because the non-wetting phase network does not satisfy the REV requirements.

Accordingly, when such a mismatch is detected, the system extends the phase/matrix model(s) by mirroring in the X and/or Y directions in block 924. Such mirroring doubles the dimension of the model in the X and/or Y dimension (for a total size that is up to 4 times the original size) while providing more pore connectivity along the mirror faces.

In block 926, the system again measures the percolation threshold using an MICP approach. As one example of how this might be done: spheres of gradually decreasing diameter are used to invade the pore space from the inlet face of the pore/matrix model. At some diameter, the spheres are able to pass from the inlet face through the model and reach the outlet face. The largest diameter (or some other measure of sphere size) that provides percolation is hereafter termed the percolation size, and the next larger diameter (i.e., the smallest non-percolating sphere diameter) is termed the connectivity threshold. The connectivity threshold is preferably at least a sphere diameter of eight or more voxels, but in any event it should be at least 3 voxels.

In block 928, the system determines whether the connectivity threshold is high enough, and if not, the system increases the sample resolution in block 930 and repeats the operations represented by blocks 904-928. The sample resolution may be increased in various ways. For example, if as part of deriving the pore/matrix model in block 904, the system scaled down high-resolution images from block 902, the system can reduce the downscaling factor. In some cases it may be possible for the system to employ image processing to increase the resolution of the images before deriving the pore/matrix model. As another option, the system may acquire new microscope images with a reduced field of view and correspondingly increased resolution. Where it is not possible to improve resolution, the system should reject the sample.

If the connectivity threshold is sufficient, the system can then engage in a relative permeability calculation in block 932 and expect to obtain reliable measurements for display to a user in block 934. In some implementations, the system uses one of the methods set forth in U.S. patent application Ser. No. 13/539,543, "Method for Simulating Fractional Multiphase/Multi-component Flow through Porous Media", filed Jul. 2, 2012 by inventors Giuseppe De Prisco, Jonas Toelke, and Yaoming Mu. Other relative permeability measurement techniques are known and can be employed. The results can illustratively be displayed in a format similar to FIG. 8A.

For explanatory purposes, the operations of the foregoing method have been described as occurring in an ordered, sequential manner, but it should be understood that at least some of the operations can occur in a different order, in parallel, and/or in an asynchronous manner.

Numerous variations and modifications will become apparent to those skilled in the art once the above disclosure is fully appreciated. For example, the foregoing disclosure describes illustrative statistics for determining an REV size, but other suitable statistics exist and can be employed. It is intended that the following claims be interpreted to embrace all such variations and modifications.

What is claimed is:

1. A multiphase permeability determination method performed by one or more computers, the method comprising:
    obtaining a three-dimensional pore and matrix model of a rock formation sample based on digital imaging of the sample using a scanning microscope;
    determining an axis of flow passing through said sample, wherein the determination is based on the orientation of the sample, formation pressure gradiens, or user specifications;
    verifying that the dimension of the model along said axis exceeds that of a representative elementary volume (REV);
    selecting a direction of the flow;
    extending said model by mirroring if pore statistics at a given saturation are mismatched for different percolating phases;
    increasing a resolution of digital imaging of the sample and repeating said obtaining, determining, verifying, selecting, extending, and increasing, if a smallest non-percolating sphere dimension is below a predetermined threshold;
    measuring relative permeability of said sample using the model; and
    providing the relative permeability measurements to a user interface for display to a user.

2. The method of claim 1, further comprising: determining absolute permeability along each axis before said determining the axis of flow.

3. The method of claim 1, wherein said selecting a direction of the flow includes:
    examining opposing faces perpendicular to the axis of flow to eliminate any face having large pores near a boundary; and
    if two faces remain, selecting the face having better pore homogeniety as a preferred inlet face.

4. The method of claim 3, further comprising:
    determining a mercury injection capillary pressure (MICP) saturation at which connectivity occurs for each direction along said axis of flow; and
    verifying that a strong directional dependence does not exist.

5. The method of claim 1, wherein said selecting a direction of the flow includes:
    determining a mercury injection capillary pressure (MICP) saturation at which connectivity occurs for each direction along said axis of flow; and
    verifying that a strong directional dependence does not exist.

6. The method of claim 1, wherein the predetermined threshold is a diameter of 3 voxels.

7. The method of claim 1, wherein said obtaining includes:
scanning a physical rock sample using the scanning microscope to obtain a three-dimensional digital image; and
deriving the pore and matrix model from the three-dimensional image.

8. The method of claim 1, wherein said pore statistics include a distribution of standard deviation of porosity.

9. The method of claim 8, wherein said pore statistics further include a distribution of standard deviation of pore surface to volume ratio.

10. A multiphase permeability determination system that comprises:
a user interface;
a memory having software; and
one or more processors coupled to the memory to execute the software, the software causing the one or more processors to:
obtain a three-dimensional pore and matrix model of a rock formation sample based on digital imaging of the sample using a scanning microscope;
determine an axis of flow passing through said sample, wherein the determination is based on the orientation of the sample, formation pressure gradiens, or user specifications;
verify that the dimension of the model along said axis exceeds that of a representative elementary volume (REV);
select a direction of the flow;
extend said model by mirroring if pore statistics at a given saturation are mismatched for different percolating phases;
increase the resolution of digital imaging of the sample and repeat said obtain, determine, verify, select, extend, and increase steps if a smallest non-percolating sphere dimension is below a predetermined threshold;
measure relative permeability of said sample using the model; and
provide the relative permeability measurements to the user interface for display to a user.

11. The system of claim 10, wherein the software further causes the one or more processors to determine absolute permeability along each axis before said determining the axis of flow.

12. The system of claim 10, wherein as part of selecting a direction of the flow, the software causes the one or more processors to:
examine opposing faces perpendicular to the axis of flow to eliminate any face having large pores near a boundary; and
if two faces remain, select the face having better pore homogeniety as a preferred inlet face.

13. The system of claim 12, wherein the software further causes the one or more processors to:
determine a mercury injection capillary pressure (MICP) saturation at which connectivity occurs for each direction along said axis of flow; and
verify that a strong directional dependence does not exist.

14. The system of claim 10, wherein said as part of selecting a direction of the flow, the software causes the one or more processors to:
determine a mercury injection capillary pressure (MICP) saturation at which connectivity occurs for each direction along said axis of flow; and
verify that a strong directional dependence does not exist.

15. The system of claim 10, wherein the predetermined threshold is a diameter of 3 voxels.

16. The system of claim 10, wherein as part of obtaining a three-dimensional pore and matrix model, the software causes the one or more processors to:
retrieve a three-dimensional image of a physical rock sample generated using the scanning microscope; and
derive the pore and matrix model from the three-dimensional image.

17. The system of claim 10, wherein said pore statistics include a distribution of standard deviation of porosity.

18. The system of claim 17, wherein said pore statistics further include a distribution of standard deviation of pore surface to volume ratio.

* * * * *